US005439481A

United States Patent [19]

Adams

[11] Patent Number: 5,439,481
[45] Date of Patent: Aug. 8, 1995

[54] SEMI-AUTOMATIC ATRIAL AND VENTRICULAR CARDIOVERTER DEFIBRILLATOR

[75] Inventor: Theodore P. Adams, Edina, Minn.

[73] Assignee: Angeion Corporation, Plymouth, Minn.

[21] Appl. No.: 96,165

[22] Filed: Jul. 22, 1993

Related U.S. Application Data

[63] Continuation-in-part of Ser. No. 974,907, Nov. 11, 1992, abandoned, and a continuation-in-part of Ser. No. 841,544, Feb. 26, 1992, Pat. No. 5,306,291.

[51] Int. Cl.$^6$ .............................................. A61N 1/39
[52] U.S. Cl. ........................................... 607/5; 607/60; 607/59
[58] Field of Search .......................... 607/5, 4, 6, 59, 60

[56] References Cited

U.S. PATENT DOCUMENTS

| | | |
|---|---|---|
| 3,738,370 | 6/1973 | Charms . |
| 3,942,536 | 3/1976 | Mirowski et al. . |
| 3,952,750 | 4/1976 | Mirowski et al. . |
| 4,499,907 | 2/1985 | Kallok et al. . |
| 4,708,145 | 11/1987 | Tacker, Jr. et al. . |
| 4,727,877 | 3/1988 | Kallok . |
| 4,774,950 | 10/1988 | Cohen . |
| 4,811,156 | 3/1989 | Kroll . |
| 4,830,006 | 5/1989 | Haluska et al. . |
| 4,870,341 | 9/1989 | Pihl et al. . |
| 4,932,407 | 6/1990 | Williams . |
| 4,964,406 | 10/1990 | Carroll et al. . |
| 4,969,463 | 11/1990 | Dahl et al. . |
| 5,014,698 | 5/1991 | Cohen . |
| 5,083,562 | 1/1992 | De Coriolis et al. . |
| 5,097,830 | 3/1992 | Eikefjord et al. ................. 607/8 |
| 5,105,809 | 4/1992 | Bach, Jr. et al. ................. 607/5 |
| 5,107,834 | 4/1992 | Ideker et al. . |
| 5,107,850 | 4/1992 | Olive . |
| 5,165,403 | 11/1992 | Mehra . |
| 5,179,945 | 1/1993 | Van Hofwegen et al. ......... 607/5 |
| 5,190,034 | 3/1993 | Sholder ............................ 607/5 |
| 5,199,429 | 4/1993 | Kroll et al. . |
| 5,207,219 | 5/1993 | Adams et al. . |
| 5,269,301 | 12/1993 | Cohen ............................. 607/6 |

OTHER PUBLICATIONS

J. L. Prevost and F. Batelli, "Sur quelque: effets des descharges electriques sur le couer des mammifers," *Comptes rendus hebdomadaires des seances de l'Academie des sciences*, vol. 129, pp. 1267, 1899.

R. A. Winkle, R. H. Mead, M. A. Ruder, et al., "Long-term outcome with the implantable cardioverter-defibrillator," *J Am Coll Cardiol.*, vol. 13, p. 1353, 1989.

M. H. Lehman, S. Saksena, "Implantable cardioverter-defibrillators in cardiovascular practice: Report of the policy conference of the North American Society of Pacing and Electrophysiology," *PACE*, vol. 14, pp. 969-979, Jun. 1991.

J. N. Wetherbee, et al., "Sequential Shocks are Comparable to Single Shocke Employing Two Current Pathways for Internal Defibrillation in Dogs", PACE, vol. 11, p. 696, Jun., 1988.

(List continued on next page.)

*Primary Examiner*—William E. Kamm
*Assistant Examiner*—Kennedy J. Schaetzle
*Attorney, Agent, or Firm*—Patterson & Keough

[57] ABSTRACT

A semi-automatic atrial and ventricular defibrillator comprising an implantable subsystem and an external programming control subsystem allowing for automatic ventricular cardioversion defibrillation countershock therapy and semi-automatic atrial cardioversion defibrillation countershock therapy. The system allows for the diagnosis of atrial and ventricular dysrhythmias and automatically treating the ventricular dysrhythmias but allowing for discretionary treatment of atrial dysrhythmias. Such discretionary control provides utility in allowing an operator including the patient, physicians, nurses, paramedics, and medical assistants to forego painful atrial defibrillation countershocks based on a medical assessment that the patient's atrial dysrhythmia is not significantly dysfunctional and amenable to less immediate and less urgent medical treatment.

10 Claims, 3 Drawing Sheets

OTHER PUBLICATIONS

J. N. Wetherbee, et al., "Nonthroctomy Internal Defibrillation in Dogs: Threshold Reduction Using a Subcutaneous Chest Wall Electrode with a Transcenous Catheter Electrode", *J. Am. Coll. Cardiol.*, vol. 10, p. 406, Aug., 1987.

J. C. Schuder, H. Stoeckle, J. A. Wes, et al, "Transthoracic ventricular defibrillation in the dog with truncated and untruncated exponential stimuli," *IEEE Trans. Biom. Eng.*, vol. BME-18 #6, pp. 410–415, Nov. 1971.

G. Weiss, "Sur la possibilité de rendre comparable entre eux les appareils survant a l'excitation electrique," *Arch. Ital. de Biol.*, vol. 35, pp. 413–446, 1901.

L Lapicque, "Definition experimentalle de l'excitabilité," *Proc. Soc. de Biol.*, vol. 77, pp. 280–285, 1909.

A. C. Guyton and J. Satterfield, "Factors concerned in defibrillation of the heart, particularly through the unopened chest," *Am J of Physiology*, vol. 167, pp. 81, 1951.

J. C. Schuder, G. A. Rahmoeller, and H. Stoeckle, "Transthoracic ventricular defibrillation with triangular and trapezoidal waveforms," *Circ Res*, vol. 19, pp. 689–694, Oct. 1966.

W. A. Tacker, L. A. Geddes, J. McFarlane, et al, "Optimum current duration for capacitor-discharge defibrillation of canine ventricles," *J Applied Physiology*, vol. 27 #4, pp. 480–483, Oct. 1969.

R. A. Winkle, "State-of-the-Art of the AICD," *PACE*, vol. 14, pp. 961–966, May 1991 pt II.

N. G. Tullo, S. Saksena, R. B. Krol, "Technological improvements in future implantable defibrillators," *Cardio*, vol, pp. 107–111, May 1990

D. P. Zipes, J. Fischer, R. M. King, et al, "Termination of ventricular fibrillation in dogs by depolarizing a critical amount of myocardium," *Am J Cardiol.*, vol. 36, pp. 37–44, Jul. 1975.

SEMI-AUTOMATIC ATRIAL AND VENTRICULAR CARDIOVERTER DEFIBRILLATOR

RELATED APPLICATION

This application is a continuation-in-part of two applications, the first of which was filed in the United States Patent and Trademark Office on Nov. 11, 1992, entitled COMBINATION ATRIAL AND VENTRICULAR IMPLANTABLE DEFIBRILLATOR, Ser. No. 07/974,907, now abandoned, and the second of which was filed in the United States Patent and Trademark Office on Feb. 26, 1992, entitled OPTIMAL ENERGY STEERING FOR AN IMPLANTABLE DEFIBRILLATOR, Ser. No. 07/841,544, now U.S. Pat. No. 5,306,291 both of which are assigned to the assignee of the present invention, and a copy of each is attached and hereby incorporated in the present application.

BACKGROUND

1. Field of the Invention

The present invention relates generally to implantable cardioverter defibrillator systems and more specifically to a semi-automatic atrial and automatic ventricular cardioverter defibrillator.

2. Background of the Invention

Irregular heart rates known as cardiac dysrhythmias generally involve sudden onset of an abnormal or pathologic rhythm disturbance involving the ventricles and atria, the chambers of the heart. Depending upon the dysrhythmia encountered, the symptoms a patient experiences can range from none at all to sudden death. The severe dysrhythmias usually involve at least the ventricles in either ventricular fibrillation or ventricular tachycardia which leads to severe compromise of the pumping capabilities of the heart. Ventricular fibrillation is the leading cause of the classic sudden death syndrome seen in heart disease patients. Due to the nature and severity of ventricular dysrhythmias, implantable automatic systems have been developed to attempt rapid intervention on behalf of the patient and return the ventricular rhythm to a normal condition. These systems are designed for automatic diagnosis of cardiac dysrhythmias and, in response, will automatically treat the dysrhythmia by delivery of a cardioversion or a defibrillation countershock.

For purpose of discussion, cardioversion should be understood to encompass all modes of treatment for all dysrhythmias, atrial or ventricular. However, due to the severe life threatening nature of ventricular fibrillation, the term defibrillation has come into use to define the specific treatment modality used to convert the ventricular fibrillation back into a more benign rhythm. Consequently, the term cardioversion is used for all other forms of cardiac dysrhythmia treatments that converts the dysrhythmia to a more benign rhythm. This use of the term cardioversion as a treatment modality applies equally well to all ventricular tachycardias, the supraventricular tachycardias, atrial flutter and even atrial fibrillation.

Isolated atrial tachycardia or fibrillation is generally not as severe as its ventricular counterpart. Ventricular fibrillation is immediately life threatening, if not reversed within several minutes the patient will die. Although ventricular fibrillation will often involve atrial fibrillation, rapid and automatic treatment is carried out with the primary purpose of treating the ventricular dysrhythmia and secondarily treating the associated atrial fibrillation.

Patients become symptomatic to lesser or greater degrees in the face of onset of atrial tachycardia or atrial fibrillation. Any particular episode of atrial dysrhythmia may lead to relatively severe symptomatology and the patient would want immediate treatment and relief. However, the degree of symptomatology suffered by the patient is dependent upon a number of factors including ventricular response time, ventricular contractility, concurrent and related disease states, diastolic filling time, and the degree of loss of cardiac output due to absence of the atrial preloading of the ventricles known as the atrial kick. All existing implantable cardioverter defibrillators (ICD) systems that are equipped to treat atrial cardioversion do so in an automatic mode. Automatic ICD systems do not take these factors into account and, thus, fail to anticipate that not all episodes of atrial dysrhythmias require immediate electrical intervention.

The patient not suffering any untoward symptomatology or, at least to them, not suffering worse than what the impending electrical shock will make them feel, may wish to avoid electrical cardioversion treatment for some occurrences of atrial dysrhythmia. Consequently, these patients might prefer to be seen and evaluated by a physician prior to undergoing treatment. Automatic ICD's offering atrial cardioversion defibrillation countershock therapy, do so without regard to the patient's clinical condition. The patient will receive a countershock for occurrences of atrial dysrhythmia even if asymptomatic. With today's automatic ICD systems, some patients may forego having an ICD implanted, despite having repeated bouts of atrial dysrhythmia, because of their concern about being suddenly shocked when still alert and asymptomatic.

SUMMARY OF THE INVENTION

The present invention embodies a novel approach to the treatment of atrial dysrhythmia via an implantable semi-automatic atrial and ventricular cardioverter defibrillator system. For the purpose of discussing and defining the present invention, semi-automatic atrial cardioverter defibrillator means a system that has two modes of operation: either an automatic mode or a manual mode for treating isolated atrial dysrhythmias. Treatment of all ventricular dysrhythmias is still carried out automatically. Because of the exigency of encountering the ventricular dysrhythmias, automatic ventricular countershock treatment takes precedence over either of the atrial modes.

An object of the present invention is to provide a system for dual chamber diagnosis and treatment of cardiac dysrhythmia.

An additional object of the invention is to allow for automatic diagnosis and treatment of ventricular dysrhythmia via the implanted cardioverter defibrillator.

A further object of this invention allows the semi-automatic atrial cardioverter defibrillator system to be controlled and programmable by an operator who is able to trigger the system manually or place it in a full automatic mode allowing the system to automatically undertake treatment of atrial dysrhythmias.

DETAILED DESCRIPTION OF THE PREFERRED EMBODIMENT

With the onset of atrial fibrillation, the ventricles respond by contraction rate acceleration due to the arrival of numerous atrial fibrillation stimuli to the AV node. This accelerated ventricular contraction rate may lead directly to worsening pump performance. The faster rate also shortens the diastolic time period, that time when the heart is at rest, during which the ventricles refill thus shortening the time the ventricles can refill for the next systolic or contraction event. Loss of the atrial kick because the atria no longer contract also contributes to a decrease in cardiac output. Poor pump mechanics, decreased diastolic filling and lack of atrial kick cause a decrease in cardiac output. It is this decrease in cardiac output which leads to the symptomatology a patient will experience with onset of atrial fibrillation.

Depending upon the patient's cardiac reserves, a loss of 10-15% of their normal cardiac output may not be symptomatic to the patient. Loss of just the atrial kick on average causes a 10-15% decrease in cardiac output. However, if the patient's cardiac reserve is already depleted secondary to other disease states, the additional sudden onset of atrial fibrillation, even though it may only lead to a 10-15% loss in cardiac output, may be sufficient to put the patient into a clinical pattern of cardiac failure such that the demands of the body are inadequately met by the diminished cardiac output.

Atrial cardioversion countershock therapy can generally be carried out in a patient awake at the time of delivery of the electrical countershock. Despite the fact that the amount of energy being delivered is only in the range of approximately 1-15 joules, the treatment remains an uncomfortable experience for any patient. If it needs to be repeated, subsequent treatments are met with apprehension and foreboding on the part of the patient. In attempts to alleviate this discomfort many physicians will employ rapid acting medicines in order to relieve the anxiety. The physician may possibly even place the patient in an unconscious state for a short period of time while the electrical energy is delivered to the heart. This approach is best utilized in conjunction with external cardioverter defibrillator systems. Existing automatic ICD's do provide the patient with the advantages of premedication. If a patient suffers a sudden onset of an atrial dysrhythmia, they generally will remain alert and cognizant of their condition. In fact they may become acutely aware that the automatic atrial cardioversion defibrillation system is charging and is going to deliver a countershock within a short period of time. Because the degree of symptomatology experienced by a patient for any given atrial dysrhythmia is variable depending upon the conditions under which the dysrhythmia occurs, automatic atrial cardioversion is not desirable for all occurrences of atrial dysrhythmia.

Figure 1:
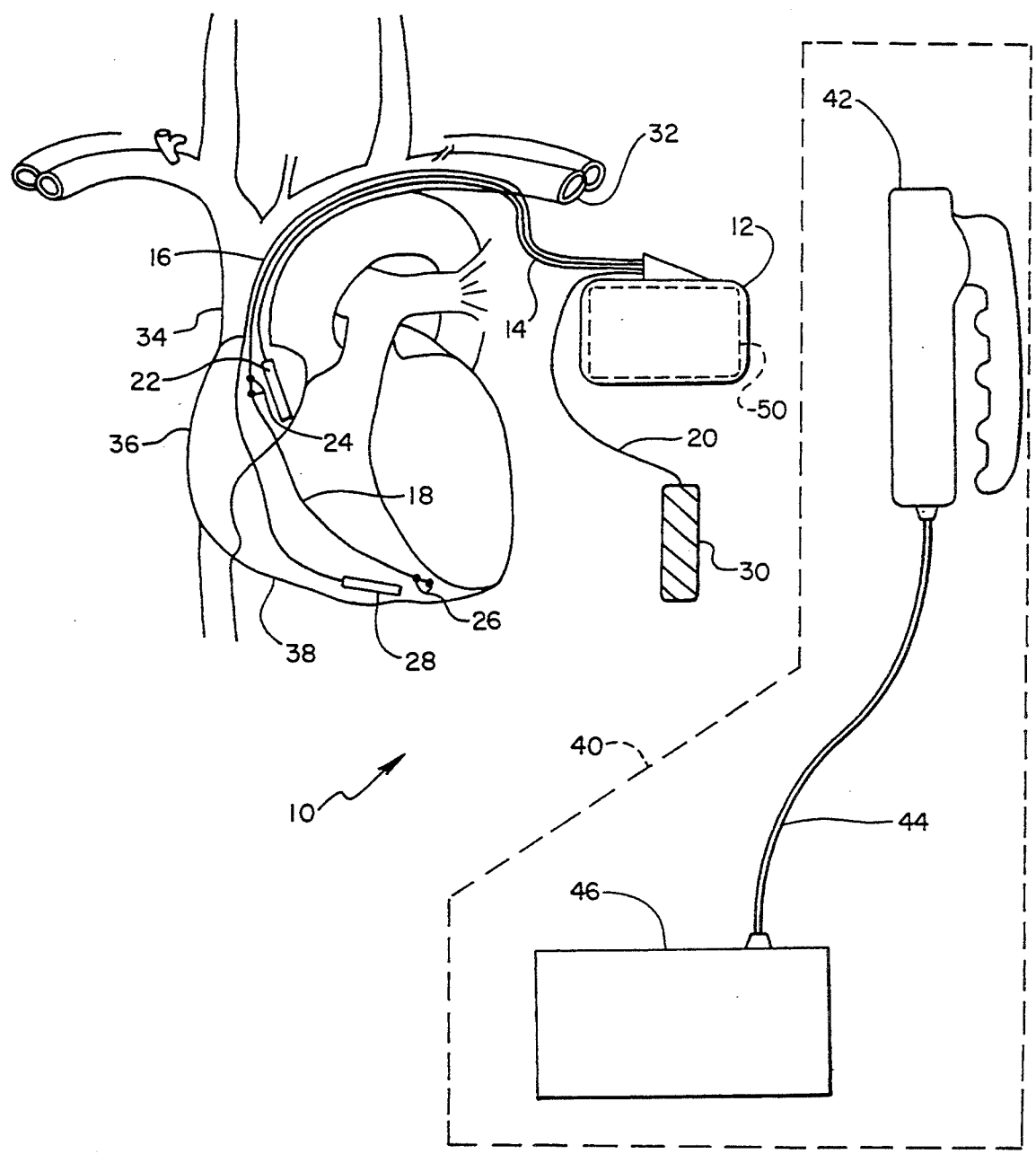
FIG. 1 is a schematic diagram of an implantable externally programmable semi-automatic atrial and ven

The present invention will now be more fully described with reference to an embodiment depicted in FIG. 1. As seen in FIG. 1, semiautomatic atrial ventricular defibrillator system 10 comprises components which are implantable within a human body and an external subsystem 40 allowing for operator programming and control.

In a preferred embodiment, the implantable components comprise: pulse generator can housing 12; a plurality of catheters 14, 16, 18, and 20 bearing a multiplicity of electrodes 22, 24, 26, 28, and 30. Pulse generator can 12, containing subsystem 50, is implanted within the human body in the subcutaneous space generally, but specifically preferring to locate it within the subcutaneous space of the anterior chest wall under either right or left clavicles of the patient. The convenience of subcutaneous placement of pulse generator can 12 allows for ready access to the venous vasculature for placement of the catheters. Catheters 14, 16, and 18 are tunneled through the subcutaneous space from pulse generator can 12 to the appropriate subclavian vein, subclavian vein 32 in this embodiment. Then using a venipuncture technique, catheters 14, 16, and 18 are introduced into subclavian vein 32 and guided through superior vena cava 34 into right atrium 36 and right ventricle 38. Catheter 14 delivers cardioversion defibrillation discharge electrode 22 to right atrium 36. Catheter 18 bears a multiplicity of electrodes 24 and 26 accomplishing atrial and ventricular sensing and pacing functions. Sensing and pacing electrodes 24 and 26 provide the input data for the diagnostic paradigms contained within pulse generator can 12. Catheter 16 delivers cardioversion defibrillation discharge electrode 28 to the apex of right ventricle 38. Additionally, catheter 20 bearing cardioversion defibrillation discharge patch 30 is implanted within the subcutaneous space similar in technique used to implant pulse generator can 12. The housing surface of pulse generator can 12 may also be configured to serve as an additional cardioversion defibrillation discharge electrode during cardioversion or defibrillation countershock therapy. The manner in which system 10 can selectively direct energy to either the atrial or ventricular chambers is disclosed in the previously identified co-pending application, U.S. Ser. No. 07/841,544, which discloses an optimal energy steering concept utilizing similar electrode placements.

External program control subsystem 40, as depicted in FIG. 1, utilizes an appropriate external wand 42 connected to external programming subsystem 46 via cable 44. External wand 42 is hand held and capable of communicating with implanted subsystem 50, containing the semi-automatic atrial programming and housed within pulse generator can 12, providing program data.

Figure 2:
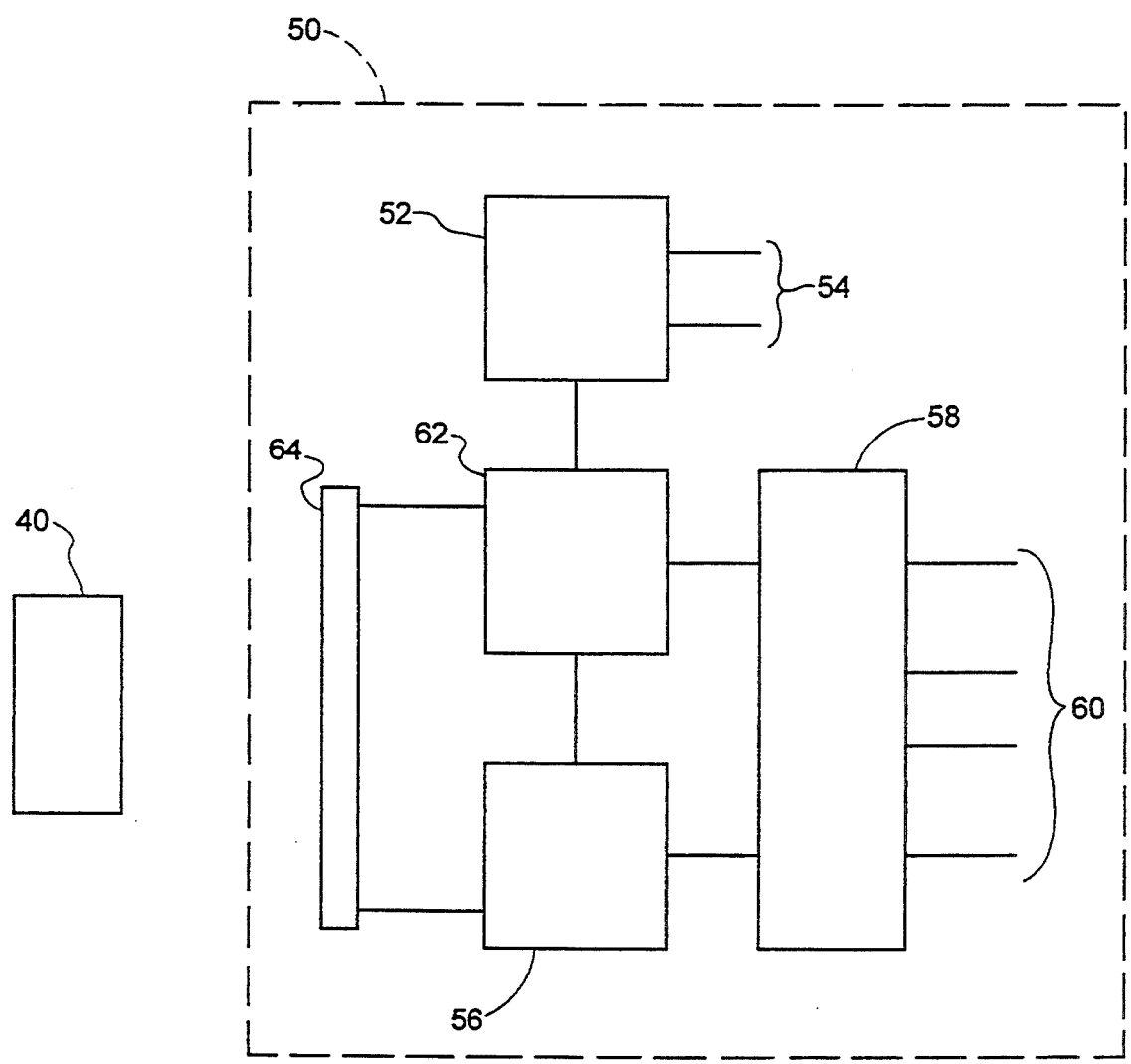
- FIG. 2 is a block diagram of an embodiment of the present invention.

Referring to FIG. 2, subsystem 50 comprises: diagnostic paradigms 52 receiving sensing from the heart via input 54; power supply subsystem 56; switching subsystem 58 to control phase, polarity, duration and direction of pacing, cardioversion and defibrillation countershocks to the heart via output 60; control interface subsystem 62; and externally programmable switching subsystem 64 capable of receiving and sending program data to and from external program controller subsystem 40 including turning on and off the semi-automatic atrial cardioversion mode in response to program commands received from external program controller subsystem 40. Externally programmable switching subsystem 64 is capable of receiving and sending program data to and from external program controller subsystem 40 utilizing electromagnetic, radio frequency, ultrasonic or magnetic communication modalities as is well known in the art.

Figure 3:
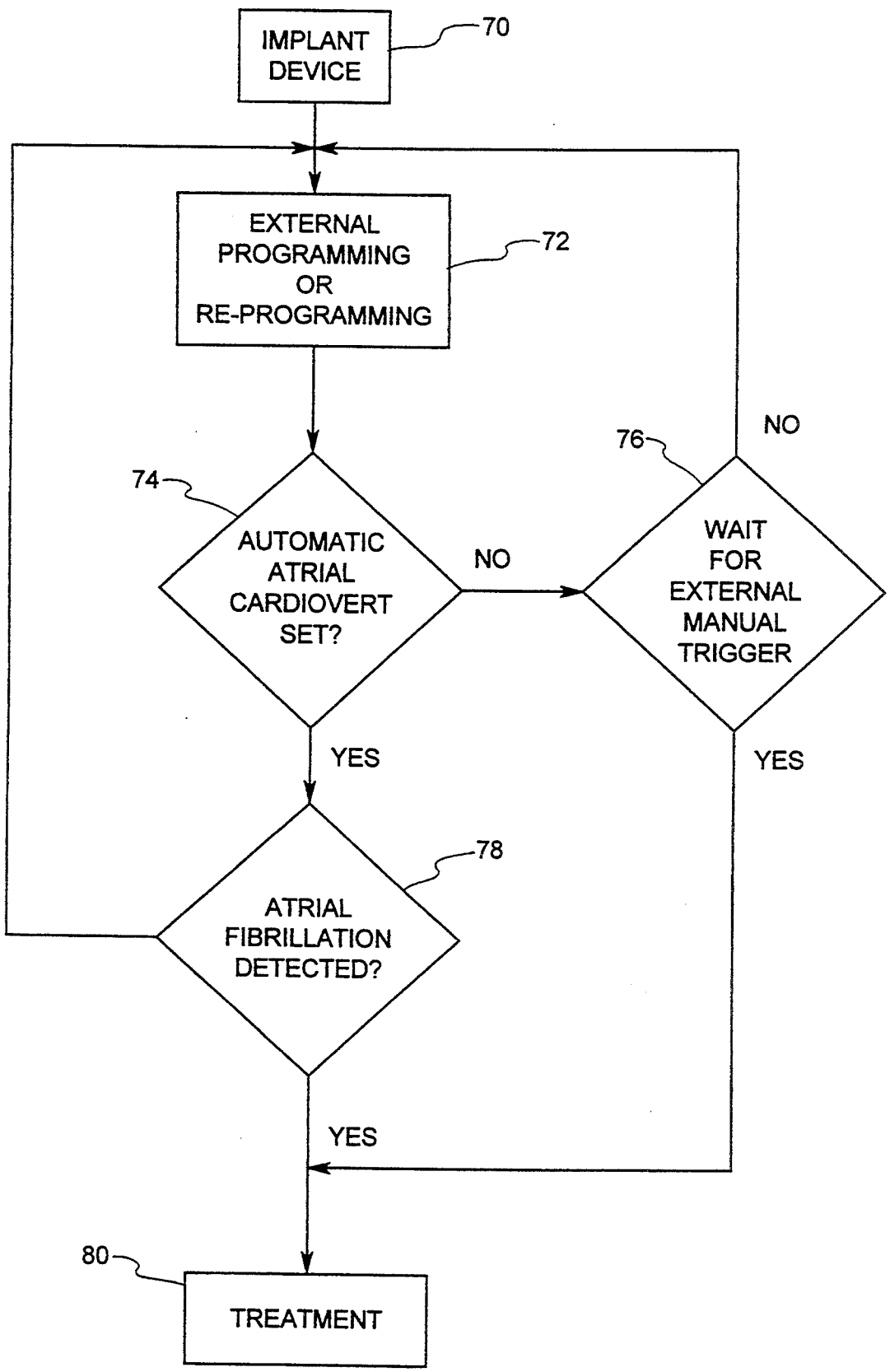
FIG. 3 is a flow diagram illustrating a method embodiment performed by an implantable cardioverter defibrillator of the present invention.

Referring to FIG. 3, following the step of implantation 70 of system 10, initial external programming at step 72 will have either set automatic atrial cardioversion or manual trigger of atrial cardioversion depicted by logic operation step 74. External re-programming at step 72 provides the ability to subsequently alter the treatment set for detection of an atrial dysrhythmia. If logic operation step 74 returns a "no" indicating that automatic atrial cardioversion has not been set, system 10 waits for an external manual trigger at step 76. If there has not been an external trigger command, system 10 next determines if external re-programming at step 72 has occurred to alter the setting of the semi-automatic atrial cardioversion mode. Upon detection of atrial fibrillation at step 78, system 10 carries out treatment step 80 by cardioverting the atria.

The externally programmable control allows a bedside operator to input commands that can turn on or turn off the semi-automatic mode of the atrial cardioversion component. It is anticipated that an operator includes anyone trained in the use of this system including the patient. In this fashion, even a patient will be able to provide interventional therapy in the event of an isolated atrial dysrhythmia and provide cardioversion countershock therapy through external wand 42. This versatility allows the operator to utilize judgment in assessing the severity of symptomatology associated with that particular atrial dysrhythmia. If the severity of dysfunction is negligible or minimal the patient may elect to forego electrical cardioversion countershock therapy and thus avoid unnecessary and painful electrical stimulation to the heart.

The patient is not the only anticipated operator of this system. It is envisioned that paramedics, medical assistants, nurses, and physicians will also have access to external program subsystem 40. Utilizing their best medical judgment they would be able to assess the patient's response and degree of disability associated with the atrial dysrhythmia and elect to intervene on behalf of the patient by altering the program of implanted subsystem 12 to enable atrial cardioversion countershock therapy.

We claim:

1. An implantable dual chamber cardioverter defibrillator apparatus for implant within a human patient, for generating and delivering cardioversion defibrillation countershocks of greater than about 0.1 joules to two or more electrodes implanted proximate the heart of the human patient, comprising:
   an implanted housing of a biocompatible material, the housing containing;
   a) means for storing an electrical charge;
   b) means for charging the means for storing to produce the electrical charge; and
   c) means for selectively controlling a discharge of the electrical charge stored in the means for storing through the two or more implanted electrodes to generate a cardioversion defibrillation countershock waveform, including:
      c1) means for detecting and automatically treating ventricular dysrhythmias without reference to an external programming stimulus;
      c2) selective means for treating atrial dysrhythmias further comprising semi-automatic means for selectively determining whether the treating of atrial dysrhythmias will be automatically initiated upon detection of an atrial dysrhythmia or manually initiated upon detection of an external programming stimulus.

2. The apparatus of claim 1 in which the sensing of the cardiac dysrhythmia comprises means for measuring a cardiac electrical signal wherein said measuring means comprises a plurality of sensing electrodes for implant proximate the heart.

3. The apparatus of claim 1 in which the selective means comprises:
   a) means, responsive to an operator for switching the apparatus from manual atrial cardioversion to automatic atrial cardioversion; and
   b) means, responsive to an operator for triggering atrial cardioversion while the implantable dual chamber system is in the manual setting.

4. The apparatus of claim 3 further comprising means for communicating with an operator, the communication means having a communication mode selected from the group of modes consisting of: magnetic, radio frequency, electromagnetic and ultrasonic modes.

5. A semi-automatic atrial and ventricular cardiac cardioverter defibrillator system for use in a human patient comprising:
   a) an implantable cardioverter defibrillator subsystem, comprising an implanted housing of a biocompatible material for implant proximate the heart of the human patient, the housing containing;
      a1) means for storing an electrical charge;
      a2) means for charging the means for storing;
      a3) means for selectively controlling the discharge of the electrical charge;
      a4) internal control means for setting semi-automatic triggering of atrial cardioversion;
      a5) internal trigger control means for allowing automatic triggering of atrial cardioversion when internal control means is set in automatic mode without reference to an external programming stimulus;
      a6) means for collection of data and communicating the data to an external receiver;
   b) an external communications subsystem comprising:
      b1) external control means for an operator to switch the apparatus back and forth from manual atrial cardioversion to automatic atrial cardioversion;
      b2) external trigger control means for allowing a system operator to trigger atrial cardioversion when internal control means is set in manual mode; and
      b3) means for receiving collected data and displaying the data for the operator to evaluate.

6. A method of operating an implantable dual chamber cardioverter defibrillator, implanted within a human patient for treating cardiac dysrhythmias of the heart of the human patient, having an electrical charge source, an electrical charge storage and an electrical discharge control means, said method comprising the device implemented steps of:
   a) programming the implanted device to effect automatic ventricular cardioversion defibrillation therapy in response to a sensing of ventricular dysrhythmia without reference to an external programming stimulus;
   b) programming the device to effect semi-automatic atrial cardioversion therapy, the semi-automatic mode including:

b1) an automatic mode for automatically effecting atrial cardioversion therapy in response to sensing of an atrial dysrhythmia;
b2) a manual mode for effecting atrial cardioversion therapy in response to an external trigger; and
c) starting the sensing of cardiac function to detect cardiac dysrhythmias.

7. The method of claim 6 further comprising the step of providing an external trigger to effect atrial cardioversion therapy.

8. The method of claim 6 further comprising the steps of capturing information, reporting information to an external source, and allowing a physician to do manual triggering.

9. An implantable cardioverter defibrillator apparatus for generating and delivering cardioversion defibrillation countershocks of greater than about 0.1 joules to two or more discharge electrodes implanted proximate the heart of a human patient in response to a sensing of a cardiac dysrhythmia in the patient, comprising:
an implanted housing of a biocompatible material, the housing containing;
a) means for storing an electrical charge;
b) means for charging the means for storing to produce the electrical charge;
c) means for selectively controlling a time truncated discharge of the electrical charge stored in the means for storing through the two or more implanted electrodes in response to the sensing of the cardiac dysrhythmia to generate a cardioversion defibrillation countershock waveform, including:
c1) means for detecting and automatically treating ventricular dysrhythmias without reference to an external programming stimulus:
c2) internal control means for receiving communication signals and triggering atrial cardioversion therapy upon receiving an external signal; and
c3) external control means for triggering cardioversion countershock therapy for atrial dysrhythmias.

10. A method of operating a dual chamber cardioverter defibrillator for treating cardiac dysrhythmias in a human patient having an electrical charge source, an electrical charge storage and an electrical discharge control means, said method comprising:
a) implanting the dual chamber cardioverter defibrillator within the human patient proximate the heart;
b) programming automatic ventricular cardioversion defibrillation therapy in response to a sensing of ventricular dysrhythmia without reference to an external programming stimulus;
c) providing manual atrial cardioversion therapy in response to an external communication signal;
d) providing internal programming control to respond to external communication signals;
e) allowing external manual control to manually trigger atrial cardioversion countershock therapy through the external communication signals; and
f) sensing to detect cardiac dysrhythmias.

* * * * *